US007622476B2

(12) United States Patent
Flieger et al.

(10) Patent No.: US 7,622,476 B2
(45) Date of Patent: Nov. 24, 2009

(54) METHODS OF USING 1-ALLYL ERGOT ALKALOID DERIVATIVES TO TREAT MIGRAINES

(75) Inventors: Miroslav Flieger, Prague (CZ); Heinz Pertz, Berlin (DE); Karel Kranda, Berlin (DE); Jan Cvak, Opava (CZ); Sven Jaenichen, Berlin (DE); Erika Glusa, Erfurt (DE)

(73) Assignee: Axxonis Pharma AG (DE)

( * ) Notice: Subject to any disclaimer, the term of this patent is extended or adjusted under 35 U.S.C. 154(b) by 0 days.

(21) Appl. No.: 10/507,577

(22) PCT Filed: Dec. 21, 2002

(86) PCT No.: PCT/DE02/04759

§ 371 (c)(1),
(2), (4) Date: Aug. 24, 2005

(87) PCT Pub. No.: WO03/076439

PCT Pub. Date: Sep. 18, 2003

(65) Prior Publication Data

US 2006/0014774 A1  Jan. 19, 2006

(30) Foreign Application Priority Data

Mar. 12, 2002  (DE) .................. 102 12 564

(51) Int. Cl.
*A61K 31/48* (2006.01)
*C07D 457/12* (2006.01)
(52) U.S. Cl. .................... 514/288; 546/68; 546/67
(58) Field of Classification Search ............... 514/250, 514/288; 546/67, 68, 69; 544/346
See application file for complete search history.

(56) References Cited

U.S. PATENT DOCUMENTS

| 3,113,133 | A | * | 12/1963 | Hofmann et al. ............ 546/69 |
| 4,898,587 | A |   | 2/1990  | Aroonsakul |
| 6,316,468 | B1 |  | 3/1999  | Maxey |
| 5,925,672 | A |   | 7/1999  | Piomelli et al. |
| 6,838,461 | B1 |  | 2/2001  | Boettcher |
| 6,218,383 | B1 |  | 4/2001  | Bencherif |

FOREIGN PATENT DOCUMENTS

| DE | 3403067 A1 | * | 8/1985 |
| GB | 2116548 A | * | 9/1983 |
| WO | WO 99/56750 |   | 11/1999 |

OTHER PUBLICATIONS

Marzoni, G. et al.: 6-Methylergoline-8-carboxylic acid esters as serotonin antagonists: N1-substituent effects on 5-HT2 receptor affinity. J. med. Chem. vol. 30, pp. 1823-1826, 1987.*

Ingelse, B.A. et al.: Ergot alkaloids as chiral selectors in capillary electrophoresis determination of the separation mechanism. J. of Chromatography A, vol. 755, pp. 251-259, 1996.*
Bisceglia, A., Cesarino, F., Cerbo, R., Runge, I., Sorrentino, R., Stocchi, F., Agnoli, A. (1990) Lisuride Prophylactic Treatment of Migraine: A Double-Blind Study at Two Different Dosages New Trends in Clinical Neuropharmacology 1990; vol. IV, N. 4: 35-40.
Somerville, B.W., Herrmann, W.M. (1978), Migraine prophylaxis with lisuride hydrogen maleate—a double blind study of lisuride versus placebo, Headache 1978; 18: 75-79.
Libermann et al., Lisuride in Parkinson's Disease and Related Disorders, in: Lisuride and Other Dopamine Agonists, D.B. Calne, R. Horowski, R. J. McDonald, W. Wuttke (Eds.), Raven-Press, New York, 1983, pp. 419-429.
Rabey et al.; A Long-Term Comparative Study of Lisuride and Levodopa in Parkinson's Disease, in: Parkinsonism and Aging, D. B. Calne et al. (Eds.), Raven-Press, New York, 1989, pp. 261-267.
Glusa, E., Markwardt, F. (1984), Interaction of lisuride with monoamine receptors on human blood platelets, Biochem. Pharmacol. 1984; 33:493-496.
Vinar et al., Antidepressant effects of lisuride are not different from effects of amitriptyline and nortriptyline, Activ. Nerv. Sup. 27, 249-251 (1985).
Bernard L. Bloom, "Behavioral Science", Community Mental Health Journal (Abstract), vol. 15, No. 3, Sep. 1979.
Munoz RF, Mrazek PJ, Haggery RJ, "Institute of Medicine Report on Prevention of Mental Disorders"—(Abstract), *Am. Psychol.* Nov. 1996; 51(11): 1130-3.
Akimov GA, "Treatment and Prevention of Diseases of the Nervous System"—(Abstract), *Zh Nevropatol Psikhiatr Im SS Korsakova.* 1967; 67(11): 1652-8.
Stephen D. Silberstein, M.D., Practice Parameter: Evidence-Based Guidelines for Migraine Headache (an Evidence-Based Review), *Neurology* 2000; 55; 754-762.
Alex, KD, Pehek EA, "Pharmacologic Mechanisms of Serotonergic Regulation of Dopamine Neurotransmission", *Pharmacol Ther.*, Feb. 2007; 113(2): 296-320 (Abstract).
Haugbol S., Pinborg LH, Regeur L, Hansen ES, Bolwig TG, Nielsen FA, Svarer C, Skovgaard LT, Knudsen GM "Cerebral 5-HT2A Receptor Binding is Increased in Patients with Tourette's Syndrom"—*Int. J. Neuropsychopharmocol.* Apr. 2007; 245-52 (Abstract).
Oh JD, Bibbiani F, Chase TN—"Quetiapine Attenuates Levodopa-induced Motor Complications in Rodent and Primate Parkinsonian Models"—*Exp. Neurol.* Oct. 2002 177(2): 557-64 (Abstract).
Seroutka SJ—"5-HT Receptors: Past, Present and Future"—*Trends Neurosci.* Feb. 1995; 18(2): 68-9) (Abstract).
Schmidt CJ, Sorensen SM, Kehne JH, Carr AA, Palfreyman MG—"The Role of 5-HT2A Receptors in Antipsychotic Activity"—*Life Sci.* 1995; 56(25); 2209-22.
Schmuck K, Ullmer C., Kalkman HO, Probst A, Lubbert H.—"Activation of Meningeal 5-HY2B Receptors: An Early Step in the Generation of Migraine Headache?"—*Eur. J. Neurosci.* May 1996; 8(5): 959-67.

(Continued)

*Primary Examiner*—Charanjit S Aulakh
(74) *Attorney, Agent, or Firm*—Wood, Phillips, Katz, Clark & Mortimer

(57) ABSTRACT

This invention relates to 1-allyl ergot alkaloids and their derivatives with selective antagonistic properties to 5-HT$_2$ receptors for the prevention of, and relief from, migraine-related headache, Parkinson's disease, disorders of the thrombocyte function, etc.

3 Claims, 1 Drawing Sheet

OTHER PUBLICATIONS

W.M. Hermann, M. Kristof and M. Sastre y Hernandez—"Preventive Treatment of Migraine Headache With a New Isoergolenyl Derivative"—*Journal of International Medical Research* (1978) 6. 476.

Brian W. Somerville and Werner M. Herrmann—"Migraine Prophylaxis with Lisuride Hydrogen Maleate—A Double Blind Study of Lisuride Versus Placebo"—*Headache* 18, 2:75-79 (1978).

R. Schade, F. Andersohn, S. Suissa, W. Haverkamp, E. Garbe—"Dopamine Agonists and the Risk of Cardiac-Valve Regurgitation"—*The New England Journal of Medicine*, Jan. 4, 2007.

A. Avila, X. Cardona, M. Martin-Baranera, P. Maho, F. Sastre and J. Bello—"Does Nefazodone Improve Both Depression and Parkinson Disease? A Pilot Randomized Trial"—*Journal of Clinical Psychopharmacology*, vol. 23, No. 5, Oct. 2003.

Bryan Roth—"Drugs and Valvular Heart Disease"—*The New England Journal of Medicine* Jan. 23, 2007.

Heike Benes—"Transdermal Lisuride: Short-Term Efficacy and Tolerability Study in Patients with Severe Restless Legs Syndrome"—*Sleep Medicine* 7 (2006) 31-35.

Katrin Bethge, Heinz H Pertz, and Klaus Rehse—"New Oxadiazole Derivatives Showing Party Antiplatelet, Antithrombotic and Serotonin Antagonistic Properties"—*Arch. Pharm. Chem. Life Sci.* 2005, 338, 78-86.

Pau Celada, M. Victoria Puig, Merce Amargos-Bosch, Albert Adell, Francesc Artigas—"The Therapeutic Role of $5HT_{1A}$ and $5-HT_{2A}$ Receptors in Depression"—*J. Psychiatry Neurosci.* 2004; 29(4).

O. Vinar, M. Zapletalek, E. Kazdova, K. Nahunek, J. Molcan—"Antidepressant Effects of Lisuride Are Not Different From Effects of Amitriptyline and Nortriptyline"—*Activ. Nerv. Sup.* (Praha), 27, 1985 No. 4.

Interaction of Lisuride with Monoamine Receptors on Human Blood Platelets—*Biochemical Pharmacology*, vol. 33, No. 3, pp. 493-496, 1984.

Cerrito F, et al., 5-HT2-receptors and serotonin release: their role in human platelet aggregation, Life Science 1993; vol. 53, pp. 209-215.

De Angelis L, 5 HT2A antagonists in psychiatric disorders, Current Opinion in Investigational Drugs 2002; vol. 3, pp. 106-112.

De Clerck F, et al., Inhibition of 5-hydroxytryptamine-induced and -amplified human platelet aggregation by ketanserin (R 41 468), a selective 5-HT2-receptor antagonist.

Agents Actions 1982; vol. 12, pp. 388-397.

De Paulis T, M-100907 (Aventis), Current Opinion in Investigational Drugs 2001; vol. 2, pp. 123-132.

Kihara H, et al., AT-1015, a novel serotonin 5-HT2 receptor antagonist, blocks vascular and platelet 5-HT2A receptors and prevents the laurate-induced peripheral vascular lesion in rats, Journal of Cardiovascular Pharmacology 2000; vol. 35, pp. 523-530.

Ninan I, et al., 5-HT2A receptor antagonists block MK-801-induced stereotypy and hyperlocomotion, European Journal of Pharmacology 1998 vol. 358, pp. 111-116.

O'Neil MF, et al., 5-HT2 Receptor Antgonism Reduces Hyperactivity Induced by Amphetamine, Cocaine, and MK-801 But Not D1 Agonist C-APB, Pharmacology, Biochemistry, and Behavior 1999; vol. 63, pp. 237-243.

Sven Jahnichen et al., Institute of Pharmacy, "Agonism at 5-HT2B receptors is not a class effect of the ergolines", European Journal of Pharmacology 513 (2005) pp. 225-228.

* cited by examiner

METHODS OF USING 1-ALLYL ERGOT ALKALOID DERIVATIVES TO TREAT MIGRAINES

This invention relates to a novel class of ergot alkaloid derivatives with selective antagonistic properties to 5-HT$_2$ receptors for the prevention of, and relief from, migraine-related headache, Parkinson's disease, disorders of the thrombocyte function, etc.

BACKGROUND AND STATE OF THE ART

Migraine is one of the most common diseases. About 10% of the population suffer from it (Worthington, 1996, Current migraine theory, Can. J. Clin. Pharm., 3, 39-51). This makes it one of the genuinely endemic diseases.

The distinguishing characteristic of classical migraine is an early stage accompanied by impaired vision, the so-called visual aura (K. Kranda, J. J. Kulikowski, 1984, Visual Aura in classical migraine, in: Neurobiology of Pain, eds. Holden & Wilmslow, MUP) that can last just minutes or for several hours. Unilateral or bilateral pulsating pain may follow the visual aura. Occurrence of the visual aura is only reported by about 20% of people suffering from migraine and defines the so-called "classical migraine" (M. L. Leone et al., 1995, A review of the treatment of primary headaches, Ital. J. Neurol. Sci., 16, pp. 577-586). The visual aura is not always followed by headache, and some patients may have pain attacks with or without the visual aura in different incidents (W. F. Stewart et al., 1992, Prevalence of migraine headache in the United States, J.A.M.A., 267, pp. 64-69); J. Olesen et al., 1994, Migraine classification and diagnosis, Neurol., 44, pp. 56-510).

Summarizing, the classical migraine consists of two main phases: a) the aural phase that may not always occur, and b) the acute, painful phase characterized by headache. This latter headache phase is characterized by throbbing pain and nausea. It is frequently accompanied by photophobia or sensitivity to noise and can last for days (P. J. Goadsby, 1997, Current concepts of the pathophysiology of migraine, Neurol. Clin., 15, pp. 27-42).

The causes and mechanisms of migraine have not been fully understood. Depression spreading in the cerebral cortex has been proposed as the initiator of the visual aura of classical migraine (Lauritzen, 1994, Brain, 117, pp. 199-210). However, theoretical considerations of the cytoarchitecture of the visual cortex make this hypothesis seem not very likely (K. Kranda, J. J. Kulikowski, 1984, Visual Aura in classical migraine, in: Neurobiology of Pain, Eds. Holden & Wilmslow, MUP).

Numerous pharmaceuticals have been proposed or are already in use for the treatment and prevention of migraine. These include analgesics, antihistamines, calcium channel blockers, and the group of serotonin agonists/antagonists such as ergot alkaloids, sumatriptan, pizotifene, and propanolol. Other pharmacological classes can potentially be used for migraine treatment and prevention such as vasodilators, neuroleptics, β-receptor blockers, and antiepileptics such as sodium valproate.

Although considerable progress has been made in migraine treatment in recent years such as using sumatriptan, a 5-HT$_1$ agonist, patients having this disease are often misdiagnosed and inappropriately treated (Worthington, 1996, Can. J. Clin. Pharm., 3, pp. 39-51). None of the available treatments causes permanent relief from migraine-type headache. For example, the disease reoccurs within a period of 24 hours in 40% of the patients that were given sumatriptan. All substances used in treatment as yet are not very specific to serotonin receptors, which causes side effects (such as coronary constriction).

5-HT$_{2B}$ antagonists are said to have great potential for the prevention and treatment of migraine. It has been observed that 5-HT$_{2B}$ agonists such as m-chlorophenyl piperazine, can cause migraine attacks in sensitive individuals (Fozard and Gray, 1989, Trends Pharmacol. Sci., 10(8), pp. 307-309). Inversely, HT$_{2B}$ antagonists can prevent a migraine outbreak (Kalkman, 1994, Life Sci., 54, pp. 641-644).

The most effective pharmaceuticals as yet in migraine prevention, methysergide, pizotifene, and propanolol, have an antagonistic effect on 5-HT$_{2B}$-Rezeptoren (Kalkman, 1994, Life Sci., 54(10), pp. 641-644). Methylergometrine as the main active metabolite of methysergide in humans also has a strong antagonistic effect on 5-HT$_{2B}$ receptors (Fozard and Kalkman, 1994, Arch. Pharmakol. 350(3), pp. 225-229).

5-HT$_{2B}$ receptors were localized in endothelial cells (intima) including the endothelial cells of blood vessels in the brain (Ullmer et. al, 1995, FEBS-Lett., 370(3), pp. 215-221) and trigger vessel relaxation by releasing nitric oxide (NO). NO may also have a part in causing migraine (Olesen et al., 1994, Ann. Neurol., 28, pp. 791-798). All migraine agents mentioned above have considerable side effects.

Another desired characteristic for an anti-migraine effect is the strong efficacy of the substances described on thrombocytes as various disorders of the thrombocyte function are known to occur with migraine. These manifest themselves by increased adhesion and aggregation during a fit, in sludging and the resulting microcirculation as well as the release of serotonin, thromboxane A and other vasoactive substances (see the overview in S. Diamond, Migraine Prevention and Management, Marcel Dekker, Basel, 1990). The effects on thrombocytes are desired whenever thrombocyte aggregation is disturbed or increased, independent of migraine.

DETAILED DESCRIPTION OF THE PREFERRED EMBODIMENTS

Figure 1:
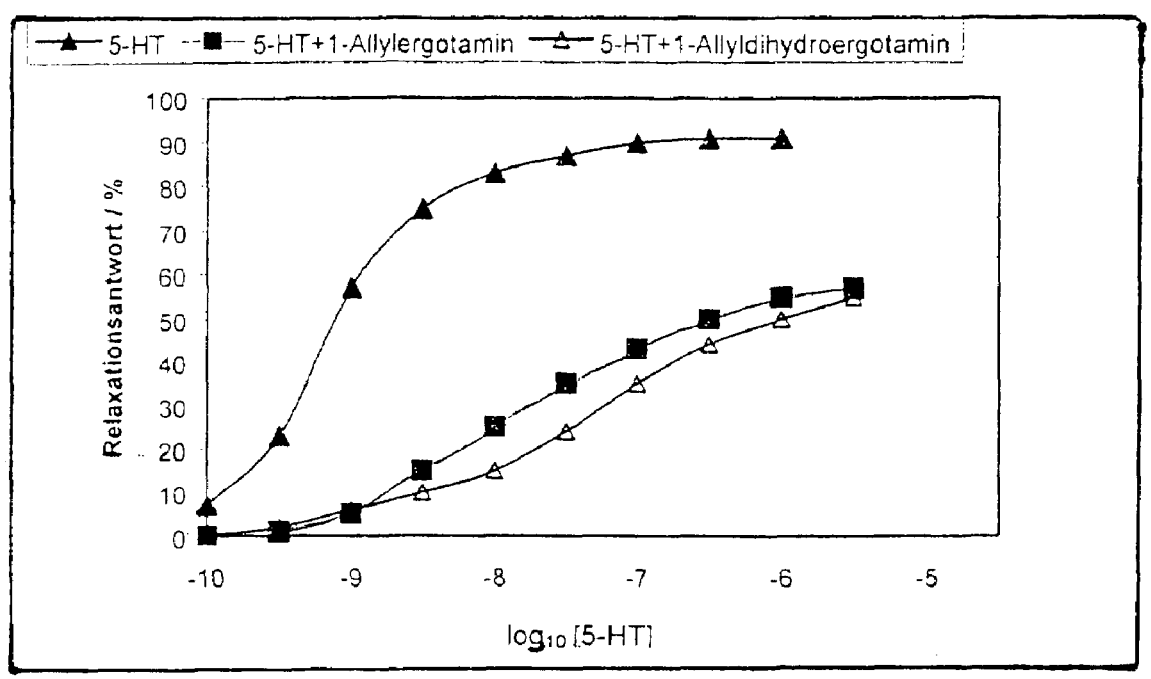
FIG. 1 is a graph showing 5-HT-induced relaxation in the absence and presence of 1-allyl ergotamine and 1-allyl dihydroergotamine.

It is an objective of this invention to provide a pharmaceutical for the prevention and relief of migraines.

According to the invention, novel allyl ergot alkaloid derivatives of the general formula (I) are provided

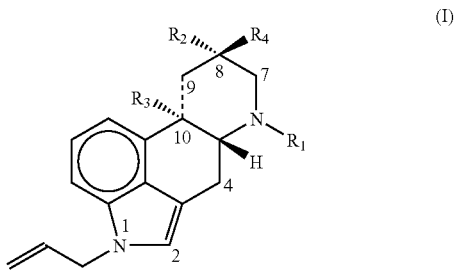

wherein
R$_1$ represents a methyl, ethyl, n-propyl, i-propyl, or allyl group,
R$_2$ is hydrogen or a NHCON(C$_2$H$_5$)$_2$ group,
R$_3$ is hydrogen or a —OCH$_3$ group, and R4 represents a methyl, ethyl, n-propyl, i-propyl, or —CH$_2$OH group, a

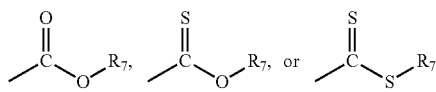

group in which R$_7$ represents an unbranched or branched alkyl group, aryl group, or aralkyl group containing 1-18 carbon atoms, a carboxy group or a group of the formula (II)

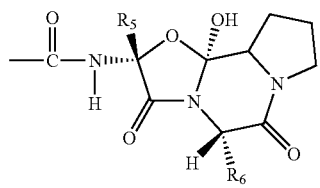

in which R$_5$ is an unbranched or branched alkyl group containing 1-4 carbon atoms and R$_6$ is an unbranched or branched alkyl group containing 1-5 carbon atoms, an aryl, an aralkyl or a —(CH$_2$)$_2$SCH$_3$ group, and the bond between C atoms 9 and 10 is either a single or a double bond while the residue R$_3$ is omitted.

In a preferred embodiment, R$_4$ is formed by a group of the formula (II) and R$_5$ represents a methyl, ethyl, i-propyl, or s-butyl group.

In another preferred embodiment, R$_4$ is a group of the formula (II) and R$_6$ represents an ethyl, i-propyl, i-butyl, s-butyl, i-pentyl, or benzyl group.

Most preferred are 1-allyl terguride, 1-allyl festuclavine, and 1-allyl dihydroergotamine.

The compounds according to the invention of the general formula (I) are produced by reacting a compound of the general formula (III)

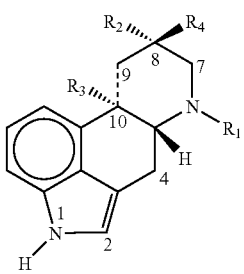

wherein

R$_1$ represents a methyl, ethyl, n-propyl, i-propyl, or allyl group,

R$_2$ is hydrogen or a NHCON(C$_2$H$_5$)$_2$ group,

R$_3$ is hydrogen or a —OCH$_3$ group, and

R4 represents a methyl, ethyl, n-propyl, i-propyl, or —CH$_2$OH group, a

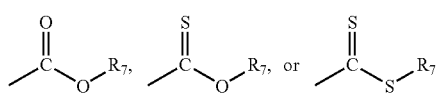

group in which R$_7$ represents an unbranched or branched alkyl group, aryl group, or aralkyl group containing 1-18 carbon atoms, a carboxy group or a group of the formula (II)

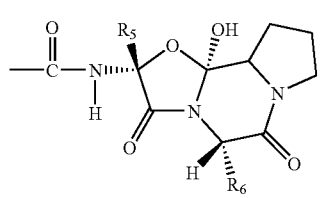

in which R$_5$ is an unbranched or branched alkyl group containing 1-4 carbon atoms and R$_6$ is an unbranched or branched alkyl group containing 1-5 carbon atoms, an aryl, an aralkyl or a —(CH$_2$)$_2$SCH$_3$ group, and the bond between C atoms 9 and 10 is either a single or a double bond while the residue R$_3$ is omitted, with allyl bromide in CH$_2$Cl$_2$, optionally adding tetraethyl ammonium hydroxide and NaOH.

The allyl ergot alkaloid derivatives of the general formula (I) of the invention may optionally be converted into an acid addition salt using the common procedures, preferably the sulphate, bisulphate, nitrate, phosphate, hydrogen phosphate, hydrochloride, hydrobromide, hydroiodide, acetate, tartrate, lactate, citrate, gluconate, fumarate, maleate, hydroxyl maleate, succinate, pamoate, benzoate, propionate, pyruvate, oxalate, malonate, cinnamate, salicylate, alkyl sulphonate, aryl sulphonate, and aralkyl sulphonate.

Another object of the invention are pharmaceuticals containing one or several allyl ergot alkaloids of the general formula (I). These alkaloids have selective antagonistic properties to 5-HT$_{2A}$ and 5-HT$_{2B}$ receptors.

Due to the allyl group inserted at N$^1$, the compounds of the invention show surprising stability against metabolic decomposition, which extends the time the pharmaceutical is effective. In addition, selective efficacy on 5-HT$_{2B}$ or 5-HT$_{2A}$ receptors is higher than for other known compounds after introducing the allyl group. Increased specificity remains for 1-allyl ergotamine and 1-allyl dihydroergotamine even when losing the partially agonistic component of the parent substances.

Selective antagonistic properties to 5-HT$_{2A}$ and 5-HT$_{2B}$ receptors makes the compounds according to the invention highly suitable as a pharmaceutical for the prevention and treatment of migraine. One or the other property in specific expression is particularly suited for acting during an acute fit in which serotoninergic nucleus raphe dorsalis is activated to an increased extent according to H. Raskin and O. Appenzeller, or in fit prevention where serotonin receptors on vessels play a specific part.

In addition, these substances have an inhibitive effect on thrombocyte aggregation. In addition to treating migraine and accompanying disorders of the thrombocyte function, the substances according to the invention are also suitable for treating disturbed or increased thrombocyte aggregation independent of migraine.

The substances according to the invention also show a high affinity to various dopamine receptors, first of all, to the D$_2$ receptor. This makes them suitable for treating Parkinson's disease and other dopamine deficiency conditions such as Restless Legs Syndrome and hyperprolactinemia. Furthermore, the substances according to the invention are suitable for use as antipsychotics due to their partially agonistic and partially antagonistic effects.

Likewise, the allyl ergot alkaloid derivatives of the general formula (I) are suited for the prevention and/or treatment of mental diseases and general diseases of the nervous system.

An object of this invention are pharmaceuticals for oral, sublingual, transdermal, rectal, topical, and parenteral (such as intravenous) application that, in addition to the common substrates and adjuvants, contain a compound of the general formula (I) or its pharmaceutically compatible acid addition salt.

The pharmaceutical according to the invention can be administered in a special depot form facilitating controlled release of the active ingredient, continuous release such as a transdermal pad, intermittent, delayed, or double release.

Dosage of the pharmaceutical according to the invention depends on the patient to be treated, the severity of the symptoms and the form of administration. The effective dose for die oral, sublingual, transdermal, rectal, topical, and parenteral administration preferably is 0.001-20 mg per kg of body weight and day. The pharmaceuticals according to the invention are produced in a known way using the solid or liquid substrates and adjuvants common in pharmaceutical engineering depending on the form of application.

Substrates and adjuvants may include binding agents, fillers, tabletting aids, diluents, solubility promoters, dyes, flavoring substances, wetting agents, emulgators, pH buffer additions, suspension aids, non-aqueous adjuvants and preservatives.

A filler may be selected from cellulose, mannitol, and lactose. Potential solubility promoters are starch, starch derivatives, and polyvinyl pyrrolidone. Adding EDTA to a solution of the active ingredient is beneficial. Sodium lauryl sulphate, lecithin, sorbitan monooleate, and gum arabic may be selected as emulgators. A suspension aid may be selected from sorbitol, methyl cellulose, gelatin, hydroxyethyl cellulose, carboxymethyl cellulose, aluminium stearate gel and hydrated nutrient fats. Potential non-aqueous adjuvants are almond oil, coconut oil, glycerin ester, propylene glycol, and ethyl alcohol. Suitable preservatives are methyl-p-hydroxybenzoate, ethyl-p-hydroxybenzoate, sodium acid sulfite, and ascorbic acid. Magnesium stearate may be used as a lubricant.

The active ingredient can be applied orally in solid form as tablets, capsules, agglomerations, powders, and lozenges or in liquid form as aqueous solution, suspension, syrup, or soluble powder. Another potential form of application would be an oral spray.

Options for parenteral application are by subcutaneous, intramuscular, or intravenous injection. The active ingredient of the general formula (I) can be a liquid suspension or a solution or can be dissolved or suspended shortly prior to injection. Addition of emulgators or wetting agents to a suspension can cause even distribution of the active ingredient in the liquid. Potential liquid substrates are saline solutions or glycerin. The preferred concentration of the active ingredient is 0.1 to 10%.

For transdermal application, the active ingredient of the general formula (I) is distributed in a carrier matrix that may be selected from mineral oil, paraffin oil, a polyacrylate, or a wax. A transdermal transport enhancer and/or structure breaker such as dimethyl sulfoxide or propylene glycol may be added.

EXAMPLES

The examples below are given to illustrate the invention without limiting it.

Example 1

Synthesis and Characterization of Compounds According to the Invention of the Formula (I)

A solution of (5R,8S,10R) terguride (4 g,11.7 mM) in $CH_2Cl_2$ (160 ml) was mixed with a 20% (v/v) solution tetraethyl ammonium hydroxide (8 ml) in 24 ml 50% (w/v) NaOH. Then allyl bromide (5 ml, 58.6 mM) is added by dropping under constant stirring. Stirring is kept up for 5 minutes after adding the allyl bromide. After separating the organic phase, the product is washed twice with water and evaporated in a vacuum. The residue was chromatographed above a silica gel column (40 g) using as $CH_2Cl_2$ eluent. The fractions with allyl terguride were dried, and the pure product was crystallized from a diethyl ether/petrol ether solution. The yield was 2.5 g of 1-allyl-(5R,8S,10R)-terguride.

All other compounds of the general formula (I) were synthesized using a similar procedure.

The structure was elucidated using mass spectroscopy and $^1H$ and $^{13}C$-NMR. The mass spectra were taken using a Finnigan MAT 90 (double-focusing, BE geometry) under the following conditions:

Ionization energy: 70 eV

Temperature of the ion source: 250° C.

Cathode emission current: 1 mA

Accelerating voltage: 5 kV; DIP: 170° C.

$^1H$ and $^{13}C$-NMR spectra:

Frequency: 400 or 100 MHz, respectively

Solvent: $CDCl_3$, 25° C.

Varian Inova 400 spectrometer

TMS standard

Results of the characterization:

A) Melting points of selective compounds according to the invention (° C.) (for trivial names and the structure of residues $R_1$-$R_6$: see Table 1):

| | |
|---|---|
| 1-Allyl festuclavine | 81-81 |
| 1-Allyl lysergol | 124-125 |
| 1-Allyluol | 203-205 |
| Ergotamine (reference) | 175-177 |
| 1-Allyl ergotamine | 179-181 |
| Dihydroergotamine (reference) | 237-238 |
| 1-Allyl dihydroergotamine | 165-167 |
| Lisuride (reference) | 173-175 |
| 1-Allyl lisuride | 72-74 |
| Terguride (reference) | 206 |
| 1-Allyl terguride | 66-67 |

B) MS data for 1-allyl terguride [m/z (relative intensity)]:

381 (10),380 (39), 308 (6), 307 (15), 265 (6), 264 (24), 263 (36), 249 (8), 221 (5), 220 (5), 209 (7), 208 (21), 207 (100), 195 (12), 194 (18), 100 (4), 74 (3).

C) NMR data for 1-allyl-(5R,8S,10R)-terguride:

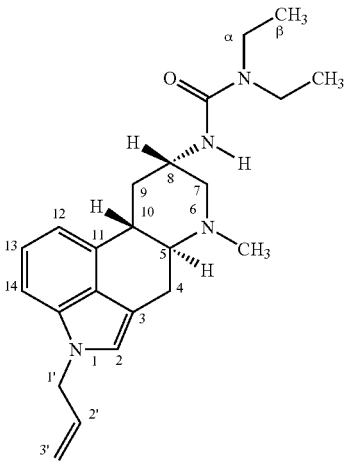

| Atom | $^{13}C$ NMR δ | mult. | $^{1}H$ NMR δ | $^{n}H$ | mult.$^a$ | J(Hz) |
|---|---|---|---|---|---|---|
| 2 | 121.73 | d | 6.774 | 1 | d | 1.7 |
| 3 | 110.84 | s | | | | |
| 4 | 26.91 | t | 2.667 | 1 | ddd | 14.6, 11.1, 1.7 |
| | | | 3.379 | 1 | dd | 14.6, 4.3 |
| 5 | 67.61 | d | 2.205 | 1 | ddd | 11.1, 9.7, 4.3 |
| 7 | 61.89 | t | 2.485 | 1 | dd | 11.7, 2.6 |
| | | | 2.874 | 1 | ddd | 11.7, 2.6., 2.4 |
| 8 | 44.95 | d | 4.282 | 1 | m | |
| 9 | 32.55 | t | 1.636 | 1 | ddd | 13.2, 13.0, 3.3 |
| | | | 2.796 | 1 | dddd | 13.2., 4.3, 2.6, 2.6 |
| 10 | 36.52 | d | 3.052 | 1 | m | |
| 11 | 133.52 | s | | | | |
| 12 | 112.83 | d | 6.888 | 1 | ddd | 6.9, 1.3, 0.9 |
| 13 | 122.73 | d | 7.158 | 1 | dd | 8.3, 6.9 |
| 14 | 107.12 | d | 7.100 | 1 | ddd | 8.3, 0.9, 0.8 |
| 15 | 133.68 | s | | | | |
| 16 | 126.71 | s | | | | |
| N—CH$_3$ | 43.39 | q | 2.416 | 3 | s | |
| N—C=O | 156.57 | s | | | | |
| 1' | 48.91 | t | 4.674 | 2 | ddd | 5.5, 1.7, 1.5 |
| 2' | 133.87 | d | 5.990 | 1 | ddt | 17.0, 10.2, 5.5 |
| 3' | 117.00 | t | 5.124 | 1 | ddt | 17.0, 1.3, 1.7 |
| | | | 5.188 | 1 | ddt | 10.2, 1.3, 1.5 |
| α | 41.06 | t | 3.250 | 1 | dq | 14.5, 7.1 |
| | | | 3.347 | 1 | dq | 14.5, 7.1 |
| β | 13.85 | q | 1.152 | 3 | t | 7.1 |
| N—H | | | 5.572 | 1 | d | 8.2 |

Example 2

Function Test Based on 5-HT$_{2B}$ Receptor Tissue

The test was an in vitro function test to characterize 5-HT$_{2B}$ receptors in a pig's pulmonary artery. The pig's pulmonary artery was prepared as follows: Small branches were dissected from the pulmonary artery and cautiously freed of organ tissue and connective tissue. Up to six rings of the artery (length 2-3 mm and width 1.5-2 mm) were hung in horizontal orientation between two L-shaped platinum hooks (150 μm in diameter) and fixed in an organ bath containing 10 ml of modified Krebs-Henseleit buffer composed as follows: 118 mM NaCl, 4.7 mM KCl, 2.5 mM CaCl$_2$, 1.2 mM MgSO$_4$, 1.2 mM KH$_2$PO$_4$, 25 mM NaHCO$_3$, and 11 mM D-glucose. A continuous flow of a gas mixture of 95% O$_2$ and 5% CO$_2$ passed through the solution which was kept at a constant temperature of 35° C. The preparations were connected to an isometric power converter (Hugo Sachs Elektronik, March, Germany), and voltage changes were continuously recorded. The constant voltage in stationary condition was adjusted to 20 mN at the beginning of each experiment. During an initial stabilization period of 60 minutes, the bath medium was replaced every 20 minutes and the voltage was repeatedly adjusted to 20 mN. The artery preparations were stimulated at 45-minute intervals once with KCl (30 mM) and three times with prostaglandin-F$_{2α}$ (PGF$_{2α}$, 3 μM) until the response by contraction was visible. The undamaged condition of the endothelium was evaluated functionally by measuring the extent of endothelium-dependent relaxation following application of bradykinin (10 nM). After the third PGF$_{2α}$-induced contraction had stabilized, the relaxation response was examined for 5-HT by determining a cumulative concentration-response curve in the absence and presence of the antagonist. FIG. 1 shows the effects on the relaxation response when adding the 1-allyl ergotamine and 1-allyl dihydroergotamine, compounds according to the invention.

The relaxation response to the test compound was examined using the same method as with 5-HT to test for agonistic activity. The concentration of the agonist was increased in increments at the time when the response signal had reached a plateau. The plateau was typically reached within 2 to 4 minutes. The relaxation effects were expressed as a percentage of the PGF$_{2α}$-induced contraction. The antagonists were added 30 minutes before the recording of the agonist concentration response curves started. The effects of the antagonists were examined in ring segments that were adjacent to the reference segments.

Die antagonistic effect of the compounds according to the invention to 5-HT$_{2B}$ receptors was proved using this method (see Table 1).

The selective effect of 5-HT$_{2A}$ receptors or 5-HT$_{2B}$ receptors, respectively, was confirmed in a comparative screening.

Example 3

Function Test Based on 5-HT$_{2A}$ Receptor Tissue

The example below describes an in-vitro function test for characterizing 5-HT$_{2A}$ receptors in rat's caudal arteries. The rat's caudal artery was prepared using the method described by Schöning (Schöning et al., 2001, Die komplexe Wechselwirkung von Ergovalin mit 5-HT$_{2A}$-, 5-HT$_{1B/1D}$-und alphai-Rezeptoren in isolierten Arterien von Ratten und Guinea-Schweinen, J. Anim. Sci., 79, pp. 2202-2209).

Male Wistar rats (250-300 g) were killed by suffocation. The anterior caudal artery was dissected fast and cleared of attached connective tissue. A stainless steel wire (0.3 mm in diameter) was introduced into the artery to strip off the endothelium. Up to 20 cylindrical segments of the artery (length 3-4 mm) were hung in horizontal orientation between two L-shaped platinum hooks (150 μm in diameter) and fixed in an organ bath containing 20 ml of modified Krebs-Henseleit buffer composed as follows: 118 mM NaCl, 4.7 mM KCl, 2.5 mM CaCl$_2$, 1.2 mM MgSO$_4$, 1.2 mM KH$_2$PO$_4$, 25 mM NaHCO$_3$, and 10 mM D-glucose. A continuous flow of a gas mixture of 95% O$_2$ and 5% CO$_2$ passed through the solution which was kept at a constant temperature of 37° C. The preparations were connected to an isometric power converter (W. Fleck, Mainz, Germany) coupled with a TSE 4711 conversion coupler and a Siemens C1016 compensograph for continuous recording of voltage modulation. The constant voltage was adjusted to 5 mN at the beginning of each experiment. During an equilibrium period of 120 minutes, the preparations were stimulated once after 60 minutes with 5-HT (1 µM).

Three cumulative concentration-response curves (CRC) were determined for each artery segment in these experiments for the study of partial agonists. The first CRC was obtained for 5-HT, the second that followed 60 minutes later for the partial agonist. Finally, the third CRC was obtained 10-15 minutes after the second CRC without washing with 5-HT and using the highest agonist concentration (0.3-3 µM). Additional experiments determined two CRCs at an interval of 60 minutes as described above. The first CRC was determined for 5-HT. The second CRC was determined to test the partial agonist in the presence of ketanserin. The preparations were incubated for 30 minutes with a ketanserin solution (3 nM).

The axial shift to the right of the curves determined in the presence of ketanserin was compared to the shift determined for the respective control preparation in the absence of ketanserin. In these experiments using ketanserin, two separate CRCs to 5-HT were obtained from each artery segment at a 90-minute interval. For the antagonists, the preparations were incubated 60 minutes prior to determining the second curve. Prazosin (0.1 µM) and cocaine (6 µM) were present in the solution during these experiments to block the $\alpha_1$-adrenoceptors and neuronal absorption of 5-HT.

The test using the method described above proved that the compounds according to the invention are partial or full antagonists of 5-HT$_{2A}$ receptors (Table 1).

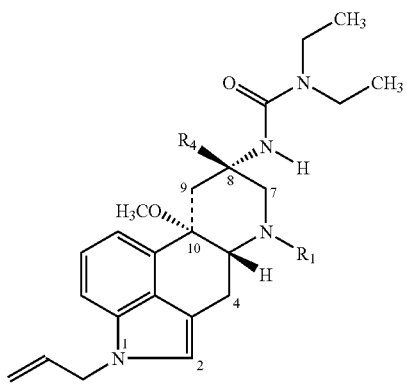

wherein
R$_1$ represents an ethyl, n-propyl, i-propyl, or allyl group,
R$_4$ represents hydrogen, a methyl, ethyl, n-propyl, i-propyl, or —CH$_2$OH group, and
the - - - bond between C atoms 9 and 10 is a single bond when the —OCH$_3$ group (C$_{10}$) is present or a double bond when the —OCH$_3$ group (C$_{10}$) is omitted and their pharmaceutically tolerable salts.

2. The method according to claim 1, wherein in the compounds of the general formula (I), R$_1$ is ethyl.

TABLE 1

Test for antagonistic effects of 5-HT$_{2A}$ and 5-HT$_{2B}$ receptors

| Compound | Structure (acc. to formula I or II) | | | | | | 5-HT$_{2A}$ | | 5-HT$_{2B}$ | | Selectivity |
| | R$_1$ | R$_2$ | R$_3$ | R$_4$ | R$_5$ | R$_6$ | Bond C$^9$—C$^{10}$ | Conc. (nM) | pA$_2$ value | Conc. (nM) | pA$_2$ value | HT$_{2A}$:HT$_{2B}$ |
|---|---|---|---|---|---|---|---|---|---|---|---|---|
| Lisuride (reference) | —CH$_3$ | —NHCON(C$_2$H$_5$)$_2$ | — | H | — | — | unsaturated | 10 | 8.60 | 1 | 10.32 | 1:52 |
| 1-Allyl lisuride | —CH$_3$ | —NHCON(C$_2$H$_5$)$_2$ | — | H | — | — | unsaturated | 30 | 8.92 | 1000 | 8.17 | 6:1 |
| Terguride (reference) | —CH$_3$ | —NHCON(C$_2$H$_5$)$_2$ | H | H | — | — | saturated | 300 | 8.38 | 10 | 8.49 | 1:1 |
| 1-Allyl terguride | —CH$_3$ | —NHCON(C$_2$H$_5$)$_2$ | H | H | — | — | saturated | 30 | 8.70 | 1000 | 7.67 | 11:1 |
| Festuclavine* (reference) | —CH$_3$ | H | H | —CH$_3$ | — | — | saturated | — | 6.63 | — | — | — |
| 1-Allyl festuclavine | —CH$_3$ | H | H | —CH$_3$ | — | — | saturated | 10-30 | 7.89 | 1000 | 6.74 | 14:1 |
| Lysergol* (reference) | —CH$_3$ | H | — | —CH$_2$OH | — | — | unsaturated | — | 6.88 | — | — | — |
| 1-Allyl-lysergol | —CH$_3$ | H | — | —CH$_2$OH | — | — | unsaturated | 3-100 | 8.45 | 1000 | 7.61 | 7:1 |
| 1-Allyluol | —CH$_3$ | H | —OCH$_3$ | —CH$_2$OH | — | — | saturated | 100 | 7.36 | 1000 | 7.03 | 2:1 |
| 1-Allyl dihydroergotamine | —CH$_3$ | H | — | Res. of formula (II) | —CH$_3$ | Benzyl | saturated | 10 | 7.65 | 30 | 9.30 | 1:45 |
| 1-Allyl ergotamine | —CH$_3$ | H | — | Res. of formula (II) | —CH$_3$ | Benzyl | unsaturated | 10 | 7.85 | — | 9.11** | 1:18 |

*Measured values from H. Pertz (1996) Planta Med. 62, pp. 387-392
**–logKp, calculated according to Kenakin

The invention claimed is:

1. A method of treating migraines in a mammal comprising the step of administering a therapeutically effective amount of the compounds of the general formula (I)

3. The method according to claim 1, wherein in the compounds of the general formula (I), R$_4$ is a hydrogen atom or a methyl group.

* * * * *

UNITED STATES PATENT AND TRADEMARK OFFICE
CERTIFICATE OF CORRECTION

PATENT NO. : 7,622,476 B2 Page 1 of 1
APPLICATION NO. : 10/507577
DATED : November 24, 2009
INVENTOR(S) : Flieger et al.

It is certified that error appears in the above-identified patent and that said Letters Patent is hereby corrected as shown below:

Title Page, Item (75), Inventors, should read: Miroslav Flieger, Prague (CZ); Heinz Pertz, Berlin (DE); Karel Kranda, Berlin (DE); Jan Cvak, Opava (CZ); Sven Jaehnichen, Berlin (DE); Erika Glusa, Erfurt (DE)

Signed and Sealed this

Second Day of March, 2010

David J. Kappos
*Director of the United States Patent and Trademark Office*